US012274916B2

(12) United States Patent
Maffei et al.

(10) Patent No.: US 12,274,916 B2
(45) Date of Patent: Apr. 15, 2025

(54) DEVICE FOR TRAINING AND MONITORING THE RESPIRATORY SYSTEM

(71) Applicant: POLITECNICO DI MILANO, Milan (IT)

(72) Inventors: Stefano Maffei, Sassuolo (IT); Aurelie Marie Glaser, Milan (IT); Massimo Bianchini, Lentate sul Seveso (IT)

(73) Assignee: POLITECNICO DI MILANO, Milan (IT)

( * ) Notice: Subject to any disclaimer, the term of this patent is extended or adjusted under 35 U.S.C. 154(b) by 0 days.

(21) Appl. No.: 18/560,027

(22) PCT Filed: May 10, 2022

(86) PCT No.: PCT/IB2022/054308
§ 371 (c)(1),
(2) Date: Nov. 9, 2023

(87) PCT Pub. No.: WO2022/238878
PCT Pub. Date: Nov. 17, 2022

(65) Prior Publication Data
US 2024/0245952 A1 Jul. 25, 2024

(30) Foreign Application Priority Data
May 11, 2021 (IT) .................. 102021000012089

(51) Int. Cl.
*A63B 23/18* (2006.01)
*A61B 5/00* (2006.01)
(Continued)

(52) U.S. Cl.
CPC ............ *A63B 23/18* (2013.01); *A61B 5/0004* (2013.01); *A61B 5/0876* (2013.01); *A61B 5/091* (2013.01);
(Continued)

(58) Field of Classification Search
CPC ....... A63B 23/18; A61B 5/0004; A61B 5/091; A61B 5/097; A61B 5/7282; A61B 5/746; A61B 2505/09
See application file for complete search history.

(56) References Cited

U.S. PATENT DOCUMENTS

| | | | |
|---|---|---|---|
| 2003/0228702 A1* | 12/2003 | Stock | A61B 5/097 436/132 |
| 2009/0312662 A1* | 12/2009 | Colman | A61B 5/097 600/543 |

(Continued)

FOREIGN PATENT DOCUMENTS

| | | |
|---|---|---|
| CN | 205127309 U | 4/2016 |
| CN | 207307086 U | 5/2018 |
| RU | 122865 U1 | 12/2012 |

OTHER PUBLICATIONS

International Search Report and Written Opinion, mailed Sep. 9, 2022, from PCT/IB2022/054308, 14 pages.

*Primary Examiner* — Puya Agahi
(74) *Attorney, Agent, or Firm* — Workman Nydegger (57) ABSTRACT

A device for training and monitoring the respiratory system comprises a main body, which defines an inhalation chamber and an exhalation chamber communicating with the external environment by means of respective external seats and interconnected by a central chamber. A mouthpiece can be further placed in fluid communication alternatively with the inhalation chamber or with the exhalation chamber by means of respective one-way valves. A measurement sensor is coupled to the main body so as to measure a value representative of the breathing process, independently monitoring the contribution of inhalation and exhalation. Such a representative value is acquired by a control unit. Lastly, an adjustable load is interposed between the mouthpiece and the central chamber.

16 Claims, 4 Drawing Sheets (51) Int. Cl.
*A61B 5/087* (2006.01)
*A61B 5/091* (2006.01)
*A61B 5/097* (2006.01)

(52) U.S. Cl.
CPC ............ *A61B 5/097* (2013.01); *A61B 5/4884* (2013.01); *A61B 5/7282* (2013.01); *A61B 5/7445* (2013.01); *A61B 5/746* (2013.01); A61B 2505/09 (2013.01); A61B 2560/0425 (2013.01); A61B 2560/0443 (2013.01); A61B 2562/0247 (2013.01); A61B 2562/18 (2013.01)

(56) References Cited

U.S. PATENT DOCUMENTS

| | | | |
|---|---|---|---|
| 2015/0258370 A1 | 9/2015 | Arkush | |
| 2016/0120462 A1* | 5/2016 | Tunnell | A61B 5/7225 600/529 |
| 2016/0136367 A1* | 5/2016 | Varney | A63B 23/18 128/202.13 |
| 2018/0147375 A1* | 5/2018 | Johnson | A61B 5/091 |
| 2019/0001187 A1* | 1/2019 | Costella | A63B 71/0622 |
| 2019/0290942 A1* | 9/2019 | Dickstein | A62B 27/00 |
| 2020/0155898 A1* | 5/2020 | Kuronen | A63B 21/00069 |
| 2023/0321375 A1* | 10/2023 | Cegla | A61M 16/20 128/200.24 |

\* cited by examiner

DEVICE FOR TRAINING AND MONITORING THE RESPIRATORY SYSTEM

BACKGROUND

The present invention relates to the technical field of medical devices with a focus on data collection and training purposes.

In detail, the present invention relates to a device for training and monitoring the respiratory system.

The care of people and health monitoring are a fundamental aspect in order to ensure a high quality of life.

In such a context, devices and techniques related to the promotion and maintenance of the well-being of the respiratory system are of particular interest.

In fact, such a system can be subject to numerous diseases which can compromise the functionality thereof and which, by making breathing difficult, become a serious obstacle to the well-being of the individual.

Even in the absence of diseases, it is still desirable to develop new technologies and procedures which allow to train and monitor the health status of such a system.

Devices are known for training the respiratory system which assist the user in a series of exercises which allow to enhance the breathing activity.

An example of such devices involves the use of a measurement sensor applied inside a chamber which has a pair of openings therein adapted to allow the passage through such a chamber of an airflow induced by the breathing activity of the user.

In fact, by means of the measurement sensor it is possible to verify the force which the user is capable of exerting during the breathing activity and this allows to perform assessments on his/her health status (for example a maximum force of particularly low value could be indicative of the presence of a certain disease in the respiratory system).

However, the device just presented, as well as the other devices known in the field, are not yet free from both structural and functional disadvantages, which still make them unsatisfactory.

In particular, the device described is not very versatile and therefore not very adaptable to the needs of the individual user.

Furthermore, such a device has an intrinsic difficulty in associating a certain pressure value measured with the inhalation or exhalation activity which generated it.

In this context, the technical task at the basis of the present invention is to propose a device for training the respiratory system which overcomes at least some of the aforementioned drawbacks of the prior art.

In particular, it is an object of the present invention to provide a device for training and monitoring the respiratory system capable of effectively and efficiently determining the pressure generated by a user while breathing regardless of the specific situation/condition of use.

The stated technical task and the specified objects are substantially achieved by a device for training the respiratory system which combines features of respiratory training and spirometry tools, comprising the technical features disclosed in one or more of the appended claims.

According to the present invention, a device for training and monitoring the respiratory system is shown.

Such a device essentially comprises a main body, a mouthpiece, a pair of one-way valves, a measurement sensor, a control unit and an adjustable load.

The main body: defines an inhalation chamber and an exhalation chamber interconnected to each other by a central chamber.

The mouthpiece is associated with the central chamber and can be placed in fluid communication with the latter.

Each chamber has a respective external seat which places it in fluid communication with the external environment.

The chambers are further placed in fluid communication with the central chamber alternately via the one-way valves.

In particular, the one-way valves are interposed one between the central chamber and the inhalation chamber and the other between the central chamber and the exhalation chamber so as to enable the passage of an airflow from the external environment to the mouthpiece, via the central chamber, solely through the inhalation chamber and from the mouthpiece to the external environment, always via the aforementioned central chamber, solely through the exhalation chamber.

The measurement sensor is coupled to the main body and is configured to measure a value representative of the user's breathing activity.

Such a representative value can comprise at least one among: a pressure value, a volume or a flow rate of an airflow inside the central chamber when the latter is placed in fluid communication with the inhalation chamber or with the exhalation chamber.

Therefore, the measurement sensor can in particular be a pressure sensor.

The control unit is coupled to the measurement sensor.

The adjustable load is interposed between the mouthpiece and the central chamber.

That is, there is a single modular load which by virtue of its specific position and configuration can act simultaneously both relative to the inhalation chamber and relative to the exhalation chamber.

The adjustable load is operable in a plurality of load configurations, each of which is adapted to determine a different resistance to the passage of air between the central chamber and the mouthpiece adapted to both inhalation and exhalation training activities.

Advantageously, the device described herein allows the precise and accurate evaluation of various parameters identifying the user's breathing activity, clearly and precisely identifying the contributions given by the user's inhalation and exhalation activity independently of one another.

The dependent claims, incorporated herein by reference, correspond to different embodiments of the invention.

Additional features and advantages of the present invention will emerge more clearly from the approximate and hence non-limiting description of a preferred but not exclusive embodiment of a device for training the respiratory system, as illustrated in the appended drawings, in which.

In the appended figures, the numerical reference 1 indicates in general a device for training and monitoring the respiratory system, to which reference is made in the following of the present description simply as device 1.

In particular, the present invention includes training the respiratory muscles, muscles involved and essential for performing the breathing activity: diaphragm, intercostal muscles, and accessory muscles, and monitoring both the strength and resistance of these muscles and the respiratory volumes.

For the purposes of the present description, the terms "training" and "monitoring" are intended to include any operation and procedure which can be carried out in order to control and/or improve the state of health and training of an individual's respiratory system.

That is, the device described herein can be used in order to monitor and/or improve the health status and functions of the respiratory system.

From a structural point of view, the device 1 comprises a main body 2, a mouthpiece 3, a pair of valves 4, a measurement sensor 5, a resistive load 7 and a control unit 6.

The main body 2 has dimensions such that it can be easily transported and such as to configure the device 1 as a portable device.

Advantageously, the main body 2 has an ergonomic shape, which can be made for example through an injection moulding process, which makes it particularly simple and easy for the user to both grasp and use.

More in detail, the main body 2 defines an inhalation chamber 2a and an exhalation chamber 2b therein.

Such chambers are distinct and separate, i.e., a direct passage of air from one to the other is not possible by virtue of the presence and the specific operating mode of the valves 4 which will be explored below.

Both chambers 2a, 2b have respective external seats which place them in fluid communication with an external environment.

That is, the inhalation chamber 2a and the exhalation chamber 2b both face the external environment via a respective external seat which operatively defines a passage through which the air can pass between the external environment and the respective chamber 2a, 2b.

The main body 2 further defines a central chamber 21 which is interposed between the inhalation chamber 2a and the exhalation chamber 2b, that is, the latter two chambers 2a, 2b are mutually separated/spaced from the central chamber 21, which (as will be explored below) can alternatively be placed in fluid communication only with one of them at a time.

Such chambers 2a, 2b can be further placed in fluid communication with the mouthpiece 3, but always via the central chamber 21.

That is, the central chamber 21 is in fluid communication with the mouthpiece 3 and allows the latter to be placed in turn in communication either with the inhalation chamber 2a or with the exhalation chamber 2b.

The adjustable load 7 is interposed between the central chamber 21 and the mouthpiece 3, its structure and operation will be explored below.

Preferably, the chambers 2a, 2b have an elongated, for example cylindrical, shape and the external seats of each chamber 2a, 2b are arranged at opposite ends with respect to the one in which they are coupled to the central chamber 21.

The central chamber 21 and the mouthpiece 3 also have a substantially cylindrical shape in which the mouthpiece 3 and one among the inhalation chamber 2a and the exhalation chamber 2b are coupled on respective opposite ends of the central chamber 2c, while the remaining chamber is coupled to a side surface thereof.

Such a specific shape is particularly adapted to establish airflows during use which meet the medical requirements for spirometry measurements.

Operatively, it therefore results that the mouthpiece 3 is configured to be placed in fluid communication with the inhalation chamber 2a or with the exhalation chamber 2b, in an independent manner through the sole central chamber 21.

In more detail, the mouthpiece 3 is thus configured to be placed in fluid communication alternatively with the inhalation chamber 2a or with the exhalation chamber 2b.

That is, the mouthpiece 3 (through which the user interacts with the device 1) can be at the same time of use of the device 1 in fluid communication only with the inhalation chamber 2a or with the exhalation chamber 2b.

The alternative connection of the mouthpiece 3 is made possible by the presence of a pair of one-way valves 4 which are interposed one between the inhalation chamber 2a and the central chamber 21 and the other between the exhalation chamber 2b and the central chamber 21.

In particular, such one-way valves 4 are installed so as to allow the passage and establishment of airflows which pass through the central chamber 21 only from the inhalation chamber 2a in the direction of the mouthpiece 3 and from the mouthpiece 3 in the direction of the exhalation chamber 2b.

That is, the one-way valves 4 are interposed between the central chamber 21 and respectively the inhalation chamber 2a and the exhalation chamber 2b so as to enable the passage of an airflow from the external environment to the mouthpiece 3 solely through the inhalation chamber 2a and from the mouthpiece 3 to the external environment solely through the exhalation chamber 2b.

Thereby, during the use of the device 1, the airflow generated by the inhalation activity of the user can only follow a path extending from the inhalation chamber 2a, through the central chamber 21 and reaches the mouthpiece 3.

Correspondingly, the airflow generated by the exhalation activity can only follow a path extending from the mouthpiece 3, through the central chamber 21 and reaches the exhalation chamber 2b.

Such a feature advantageously allows to keep the airflows generated by the user's breathing separate, thus allowing to carry out precise measurements and evaluations related to the two individual activities (inhalation and exhalation) independently and without the risk of interference between the two.

Furthermore, the specific positioning of the valves 4 ensures the creation of a controlled and stable environment inside the central chamber 21 (allowing particularly precise and accurate measurements), without at the same time hindering the establishment of the normal airflows deriving from the user's breathing activity.

Advantageously, the device 1 can further comprise at least one mouthpiece attachment 3a reversibly couplable to the mouthpiece 3, which can be held in the mouth by the user during the operation of the device 1.

Advantageously, the removability and therefore the replaceability of the mouthpiece attachment 3a allows the subsequent use of the device 1 even for long periods and by different users in a particularly safe and hygienic manner but also allows coupling mouthpiece attachments 3a having different structures, sizes and shapes.

In particular, such mouthpiece attachments 3a can comprise medical mouthpiece attachments, sports mouthpiece attachments, masks or similar devices structured so as to allow the user to inhale inside the device 1.

Furthermore, the presence of the mouthpiece attachment 3a prevents the user from applying a pressure directly on the mouthpiece 3 with the mouth which could generate reading errors by the measurement sensor 5.

The device 1 can further comprise at least one filter interposed between the mouthpiece 3 and the central chamber 21 and/or between the central chamber 21 and at least one among the inhalation chamber 2a and the exhalation chamber 2b.

Such filters carry out the function of preventing the entry of contaminants present in the air inside the user's respiratory tract or the transfer to the device 1 of contaminants present in the user's breath.

In the first case, particular reference is made to contaminants such as dust and allergens, while in the second case, by way of example, bacteria and viruses are indicated.

Advantageously, the filters are also removable and can be removed from the device 1 and replaced as necessary.

The measurement sensor 5 is coupled to the main body 2, which is configured to measure a value representative of the breathing activity of the user inside the inhalation chamber 2a and inside the exhalation chamber 2b, in particular during the use of the device 1.

Such a representative value can comprise by way of example at least one among: a pressure value, a volume or a flow rate of an airflow generated by the breathing activity of the user and independently measured/evaluated for the inhalation and exhalation activity.

In accordance with an aspect of the present invention, the measurement sensor 5 comprises a measurement sensor made by means of a differential piezoelectric pressure sensor.

In general, the measurement sensor 5 comprises a first terminal configured to acquire a first measurement signal in the central chamber 21 and a second measurement terminal configured to acquire a second measurement signal at the mouthpiece 3.

Such measurement signals also contain relevant information identifying the user's breathing activity.

In particular, the representative signal is calculated as a function of a difference between the first and the second measurement signal.

In more detail, from the structural point of view, the first measurement terminal is positioned at a surface of the adjustable load 7 facing the mouthpiece 3 and the second measurement terminal is positioned at a surface of the adjustable load 7 facing the central chamber 21.

Under normal conditions, the breathing activity of an individual generates low pressure values, i.e., usually comprised between 200 $cmH_2O$ and less than 100 $cmH_2O$ (it should be recalled that 100 $cmH_2O$ correspond to 9.8 Kpa).

Therefore, given the scale of the values to be measured, their absolute measurement is difficult and would require the use of expensive and complex instruments in order to obtain sufficiently precise results.

On the contrary, the piezoelectric differential measurement sensor allows to evaluate not so much the absolute value of the pressure, but its variations during the use of the device 1, thus allowing to acquire precise, reliable and significant results even with a relatively simple structure.

Advantageously, the measurement sensor 5, regardless of its specific type, is waterproof or waterproofed.

In fact, since such measurement sensor 5 is inserted inside the inhalation and exhalation chambers 2a and 2b, it is exposed in a continuous and potentially even prolonged manner to the moisture normally present in the user's breath and in the air.

In this context, the waterproofing of the measurement sensor 5 thus allows to extend the useful life thereof, preventing moisture from damaging it.

As indicated, the adjustable load 7 is interposed between the central chamber 21 and the mouthpiece 3.

The adjustable load 7 is operable in a plurality of load configurations, each of which is adapted to determine a different resistance to the passage of air and to carry out both inhalation and exhalation training activities.

In other words, the adjustable load 7 represents an element of the device 1 aimed at determining the ease of passage of air through the central chamber 21 to and from the inhalation and exhalation chambers 2a, 2b.

It is thereby possible to train the respiratory system and/or monitor the performance thereof in situations of effort in which resistance, through the adjustable load 7, to the breathing activity of the user is actively opposed.

Figure 1:
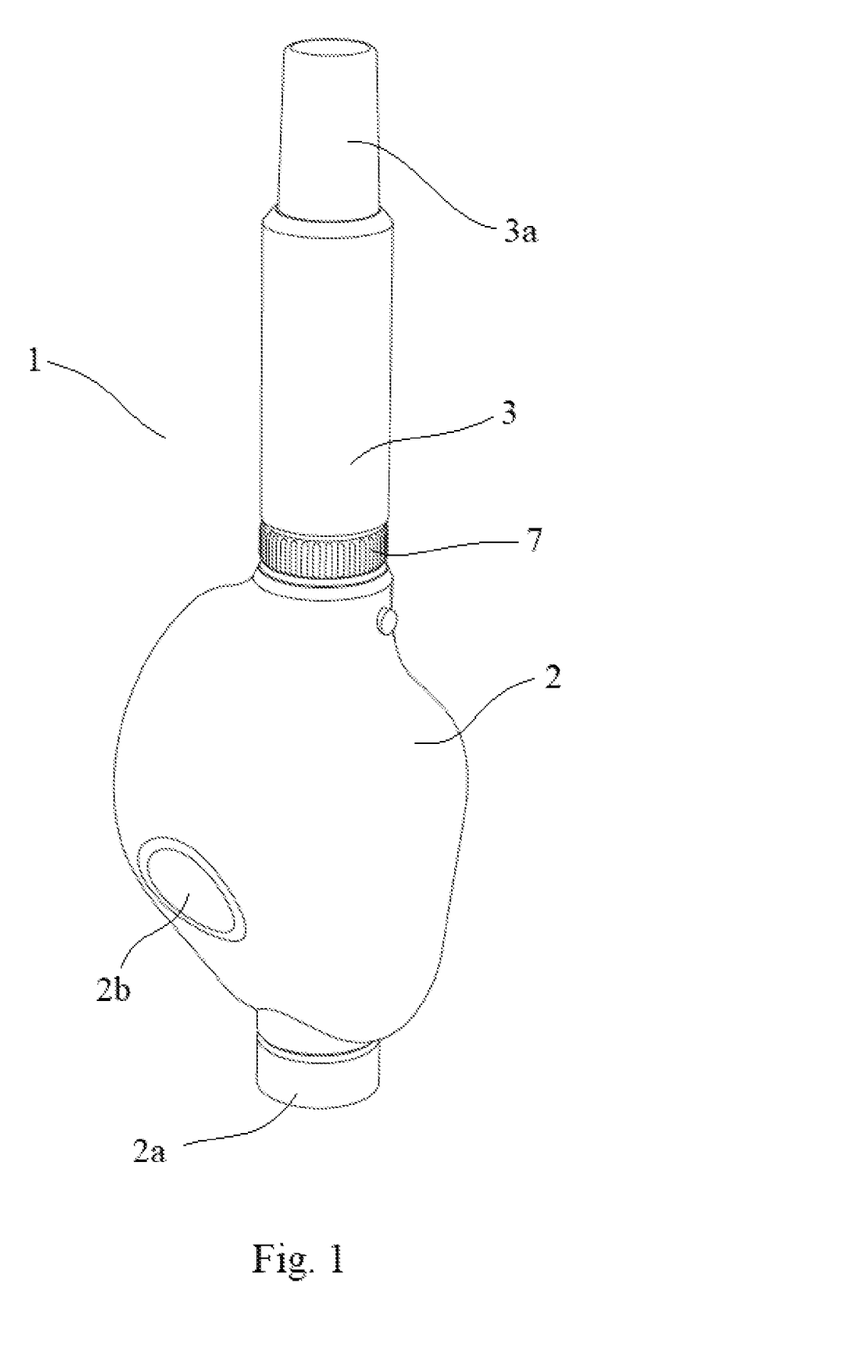
FIG. 1 shows a view of the device according to the present invention.
Figure 2:
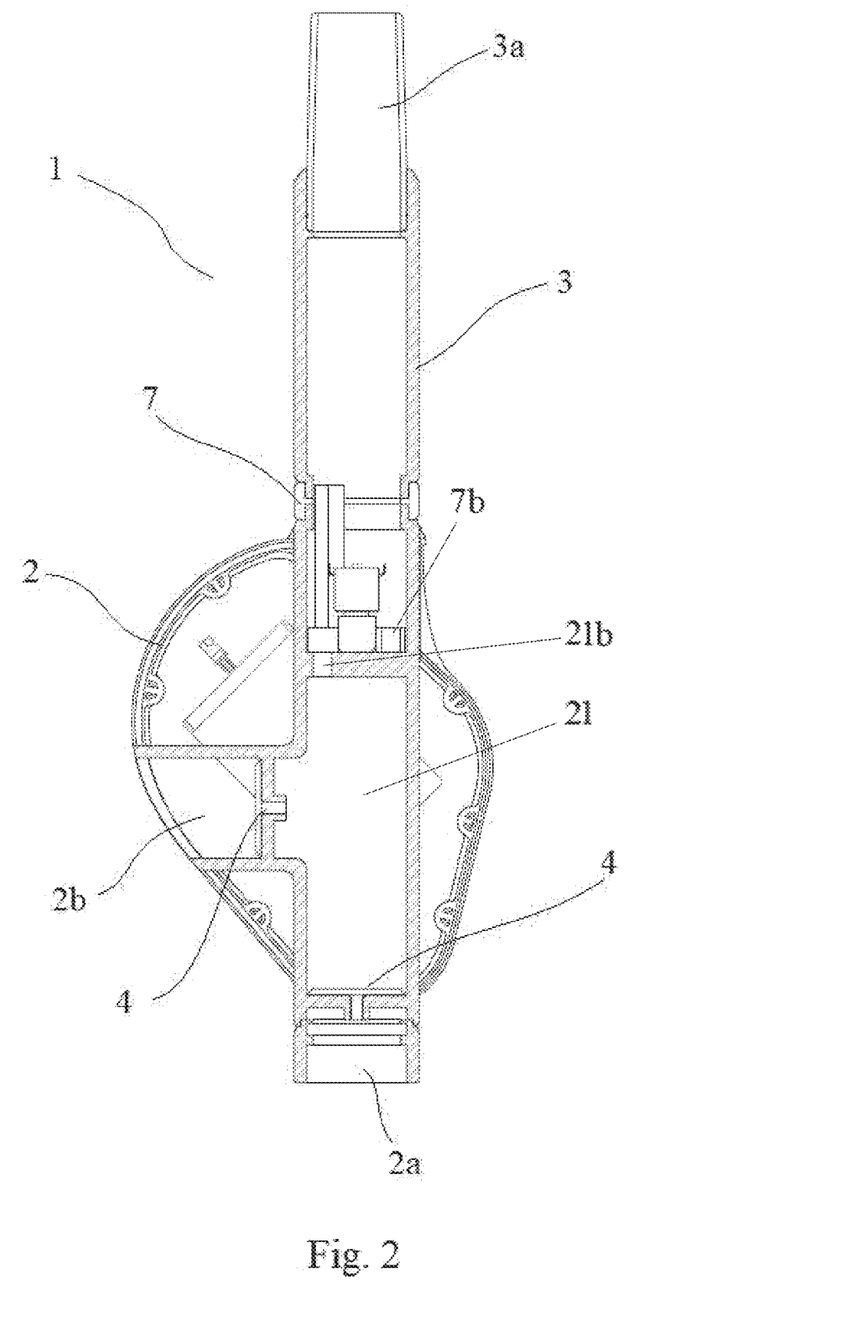
FIG. 2 shows a section of FIG. 1.
Figure 3:
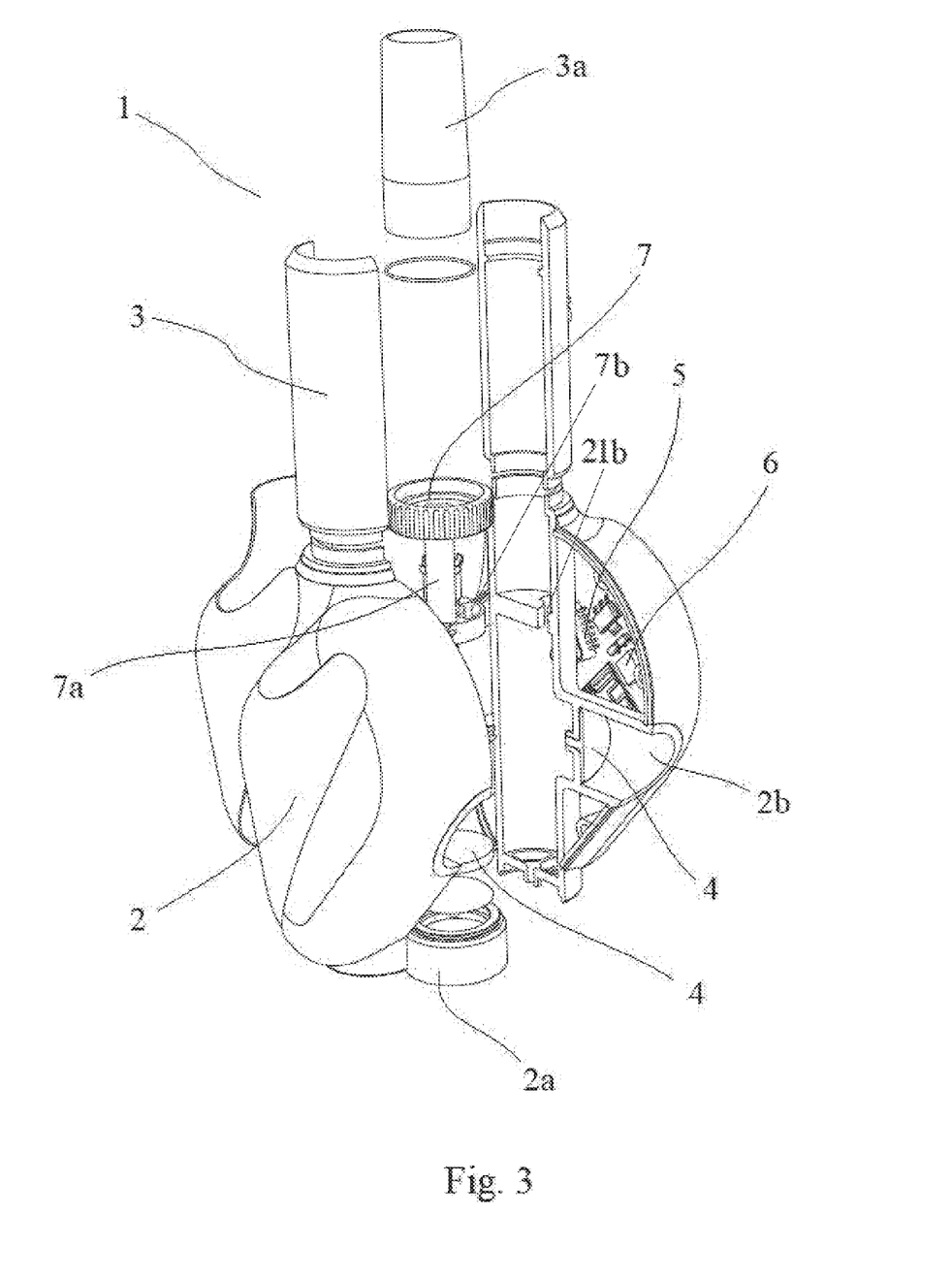
FIG. 3 shows in detail some of the components of the device.
Figure 4:
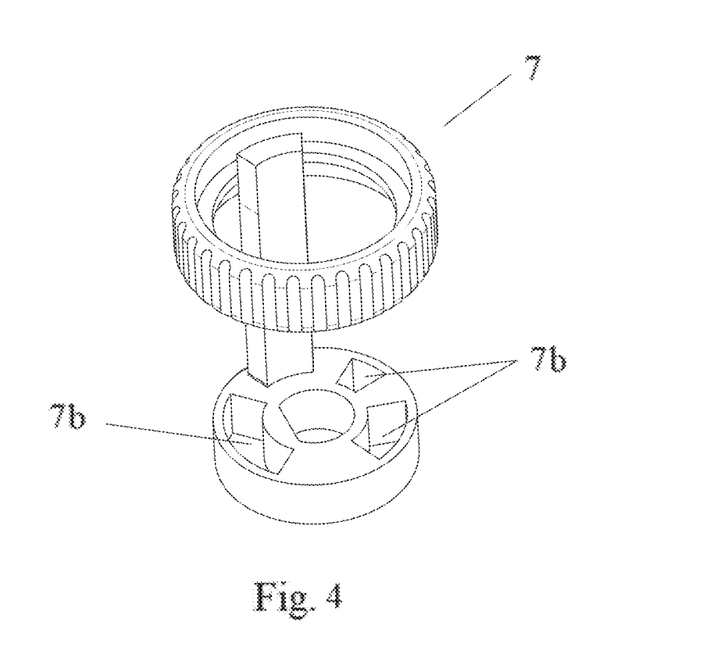
FIG. 4 shows in detail an adjustable load according to the present invention.

In detail, the adjustable load 7 comprises a load body 7a coupled to the main body 2 and having a plurality of holes 7b of different sizes.

Preferably, such holes have a shape such as to define or contribute to defining respective Venturi tubes when in use.

Thereby, after having crossed the modular load 7, the airflow moves with a laminar regime, thus allowing the measurement sensor 5 to acquire the representative value in a particularly precise and accurate manner.

Such holes 7b are selectively overlappable with a passage section 21b which places the central chamber 21 in fluid communication with the mouthpiece 3 so as to effectively vary the passage section 21b through which the airflow can flow during the breathing activity.

That is, the passage section 21b which allows the flow of the airflow to and from the mouthpiece 3 relative to the inhalation chamber 2a and the exhalation chamber 2b has a maximum size, preferably a diameter in the case of holes 7b of circular shape, which is variable and determined by the size of the specific hole 7b which is activated by overlapping the passage section 21b.

Preferably, the holes have a size range which is increasing from a minimum value of 2 millimetres in diameter.

Operatively, smaller holes 7b will make the passage of air more difficult, while larger holes 7b will oppose a lower resistance during the use of the device 1 and it will therefore be easier for the user to inhale and exhale.

In detail, for respiratory tests of type VT (tidal volume), FEV1 (forced expiratory flow) FVC (forced vital capacity), VC (vital capacity) the use of larger holes ensures the creation of a laminar flow which does not influence the pressure inside the central chamber 2c.

In contrast, for the execution of MIP (maximal inspiratory pressure) and MEP (maximal expiratory pressure) tests, the use of smaller holes (diameter) equal to 2 mm make it optimal for the execution of this type of test.

In more detail, the load body 7a is rotatably movable relative to the main body 2b so as to place, in each load configuration, a respective hole 7b over the passage section 21b.

Alternatively or additionally, the adjustable load 7 comprises two load bodies 7a, in particular a first load body 7a coupled to the external seat of the inhalation chamber 2a and a second load body 7a coupled to the external seat of the exhalation chamber 2b and configured to modulate a resistance to the passage of air from the external environment with respect to such chambers 2a, 2b.

It is thereby possible to independently determine the specific load configuration taken on by the two chambers 2a, 2b during the use of the device 1.

If both the load bodies 7a associated with the individual chambers and the one associated with the passage section 21b are present, it is observed that the load body 7a associated with the passage section 21b determines a common resistance to which both the inhalation and exhalation processes will be subject, while the individual load bodies 7a associated directly with the individual inhalation chambers 2a or exhalation chambers 2b allow to modulate any specific resistance values for the respective activities in a particularly fine and precise manner.

Preferably, the adjustable load 7 is operable, i.e., each of its adjustable loads 7a is operable, between a maximum load configuration in which it exerts a resistance to the passage of air that is equal to or less than 270 $cmH_2O$ and a minimum load configuration in which it exerts a resistance to the passage of air that is equal to or greater than 0 $cmH_2O$.

Such a wide range of resistance values makes the device 1 particularly versatile and adapted to be used in a wide range of different situations, making it easily adaptable both for training operations of the respiratory system and to allow evaluations of its functions in the clinical field.

Advantageously, the device 1 can further comprise an encoder applied to the load body 7a and configured to measure the angular position thereof.

It follows that the position of the load body 7a is continuously monitored and can be advantageously transmitted to the control unit 6 in the form of a load signal which allows to uniquely identify the load configuration taken on by the adjustable load 7.

That is, by means of the encoder, the control unit 6 can detect at any time the angle of rotation of the main body 7a and then deduce which hole 7b is active, i.e., it is determining the size of the passage section 21b through which the airflow generated by the breathing activity of the user passes.

This thereby allows to automatically and autonomously determine the specific resistance which is being opposed to the user's breathing activity at any time.

More generally, the control unit is mainly configured to acquire the information provided by the encoder and exploit it to more accurately analyse and/or evaluate and/or interpret the representative value received by the measurement sensor.

The continuous monitoring of the applied load value thus allows a high measurement accuracy to be ensured and the actual relevance of the measured values for the representative value to be correctly assessed at all times.

In general, the control unit receives the representative value during the use of the device 1.

Such a representative value indicates overall the effort which the user is exerting to inhale and exhale respectively, thus allowing an assessment to be made on his/her health status and in particular on the health status of his/her respiratory system.

In fact, healthy individuals will be able to apply greater pressures than individuals suffering from diseases affecting the respiratory system such as to affect the operation thereof.

Furthermore, the use of the device 1, especially in the presence of the adjustable load 7, allows to perform training cycles aimed at improving the performance of the respiratory system, for example by repeating inhalations/exhalations performed with a certain frequency or with the achievement of certain target pressure values.

The device 1 can also comprise further sensors and/or the measurement sensor 5 can be configured for the measurement of further values, in particular values related to biometric parameters of the user.

Advantageously, the pressure value obtained by the control unit can be displayed via a screen included in the device 1 (in particular coupled to the main body 2), or connectable thereto.

Such a screen can further display any information which can be processed by the device 1 via its control unit 6 and also general information about the operating status of the device 1.

Such information, i.e., the pressure value and any further processable information, can also be stored on a reversibly readable storage medium couplable to the main body 2.

That is, the readable storage medium can be coupled to the main body and consequently be interfaced with the control unit 6 to exchange data/information with the latter, in particular to store a plurality of pressure values.

The readable storage medium can also associate the pressure values acquired by the control unit 6 with further identification data, for example the date and time when such pressure values were acquired.

By way of non-limiting example, the readable storage medium can comprise an SD card.

In particular, the coupling of the various removable elements to the device 1 can be obtained by inserting them inside special housings made in the main body 2 and closed/closable by, for example, snap closures, specifically snap-fit type closures.

The device 1 can also comprise a signaller configured to alert a user of an error condition of the device 1 itself. Preferably, the error condition is determined by a malfunction of the measurement sensor 5.

That is, whenever the measurement sensor 5 does not operate correctly and/or is damaged, the indicator generates an alarm which notifies the user. In particular, the alarm can be displayed on the screen if present or the signaller can comprise one or more among an acoustic signaller, an optical signaller or a vibration motor which can be activated according to specific protocols (combinations of sounds, lights, vibrations) to alert the user of respective problems in the operation of the device 1. Advantageously, the device 1 can further comprise a transmission module configured to transmit the pressure value acquired by the control unit 6 to a remote terminal such as a computer, a smartphone or a remote database.

Preferably, the transmission occurs by means of a wireless communication protocol which can for example comprise at least one among: Wi-Fi®, Bluetooth® or a cellular network.

Therefore, the transmission module manages and coordinates, in addition to sending to the remote terminal, also the possible reception not only of the pressure value, but of any processed/processable information by the control unit 6.

It is thereby possible to send information related to the use of the device 1 remotely, for example to a facility of medical personnel, who can analyse such data and formulate specific diagnoses and/or training plans for the individual user.

Furthermore, the device 1, specifically the transmission module, is interfaceable with a remote database, preferably a computing cloud, in order to store the representative value and its variations over time and in successive uses of the device and acquire from said remote database one or more items of operational information.

Preferably, said operational information comprising at least one training regime defined at least by the number of uses of the device 1 in a predetermined interval of time and/or by the load configuration for each use of the device 1.

That is, the device 1 can be interfaced with a remote database which can define an online platform through which a plurality of pieces of information which can be used by the user to manage the operation of the device 1 is collected and acquired.

Such a database can also provide additional customisation options by virtue of which the individual training regimes can be customised according to both the information derivable from the representative value and the biometric and personal data of the user, which can be provided by the user himself/herself or be acquired from healthcare facilities.

Advantageously, the device 1, in particular the control unit, is in real-time communication with the database within which the relevant medical and biometric information of the user is inserted (age, gender, height, weight, medical conditions).

This information allows to compare the data acquired in real time by the measurement sensor 5 with corresponding values saved, stored, archived in the database and/or with medically predictable values for the training and monitoring procedures of people belonging to the same category (in terms of age, medical conditions or similar classification parameters) of the user. The comparison of such data allows to evaluate both a health status of the user (for example values which differ from those provided for the same category of people may indicate the onset of a disease) and allow to create custom training regimes (in particular from the point of view of the selection of the load to be applied by means of the adjustable load 7) adapted according to the specific needs of the user as a function of the information contained in the database regarding the performance of users belonging to similar categories.

In general, the remote database can provide a calendar service in which it provides daily or at regular and preset intervals indications to the user regarding the execution of specific training regimes or use regimes of the device 1 aimed at collecting pressure values which can be exploited for diagnostic purposes.

Such a platform or database can also be remotely accessible by facilities and medical personnel who, as already indicated, can use the information collected for stable training plans or determine the occurrence of pathological states in the user.

The control unit 6 can also process the representative values so as to determine, through the use of statistical and predictive algorithms, possible threshold values identifying a correct execution of specific training regimes so as to be able to provide the user with feedback on their correct execution, as well as generate and possibly send an alert signal to the remote database (making it identifiable, for example, by the healthcare facility which has prepared such a training regime) if the deviation is greater than a predefined limit value.

Advantageously, the present invention achieves the proposed objects overcoming the drawbacks complained of in the prior art by providing the user with a device for training the respiratory system which ensures precise and accurate measurements of the effort exerted by the user to breathe, further presenting a high versatility which allows the use thereof in a wide variety of situations.

The invention claimed is:

1. A device for training and monitoring a respiratory system, the device comprising:
a main body defining:
an inhalation chamber and an exhalation chamber having respective external seats adapted to place the inhalation and exhalation chambers in fluid communication with an external environment; and
a central chamber interposed between the inhalation chamber and the exhalation chamber;
a mouthpiece associated with the central chamber and configured to be placed in fluid communication alternatively with the inhalation chamber or with the exhalation chamber through said central chamber;
a pair of one-way valves interposed between the central chamber and respectively the inhalation chamber and the exhalation chamber so as to enable a passage of an airflow from the external environment towards the mouthpiece solely through the inhalation chamber and from the mouthpiece to the external environment solely through the exhalation chamber;
a measurement sensor coupled to the main body and configured to independently measure a value representative of breathing activity of a user when said central chamber is placed in fluid communication with the inhalation chamber or with the exhalation chamber;
an adjustable load interposed between the mouthpiece and the central chamber, said adjustable load being configured to operate in a plurality of load configurations each of which is configured to present a different resistance to the passage of air between the central chamber and the mouthpiece for performing both inhalation and exhalation exercises; and
a control unit coupled to the measurement sensor in order to acquire said representative value;
wherein said adjustable load comprises a load body coupled to the main body and having a plurality of holes of different sizes, said load body being rotatably movable relative to the main body so as to place, in each load configuration, a respective hole over a passage section between the central chamber and the mouthpiece.

2. The device according to claim 1, wherein the measurement sensor comprises:
a first measurement terminal configured to acquire a first measurement signal in the central chamber;
a second measurement terminal configured to acquire a second measurement signal at the mouthpiece;
a representative signal being calculated as a function of a difference between the first and the second measurement signal,
said representative signal comprising at least one among: a pressure value, a volume or a flow rate of an airflow.

3. The device according to claim 2, wherein the first measurement terminal is positioned at a surface of the adjustable load facing the mouthpiece and the second measurement terminal is positioned at a surface of the adjustable load facing the central chamber.

4. The device according to claim 1, wherein said holes define respective Venturi tubes.

5. The device according to claim 1, wherein the adjustable load is operable between a maximum load configuration in which it exerts a resistance to the passage of air that is equal to or less than 270 $cmH_2O$ and a minimum load configuration in which it exerts a resistance to the passage of air that is equal to or greater than 0 $cmH_2O$.

6. The device according to claim 1, wherein the measurement sensor comprises a piezoelectric differential measurement sensor.

7. The device according to claim 1, wherein the measurement sensor is waterproof or waterproofed.

8. The device according to claim 1, further comprising an encoder applied to the load body and configured to transmit to the control unit a load signal identifying the load configuration taken on by the adjustable load.

9. The device according to claim 1, further comprising a transmission module configured to transmit the representative value to a remote terminal, by means of a wireless communication protocol, the wireless communication protocol comprising at least one among: Wi-Fi®, Bluetooth® and a cellular network.

10. The device according to claim 1, further comprising or connectable with a screen configured to display at least the representative value.

11. The device according to claim 1, further comprising a reversibly readable storage medium coupled to the main body and interfaceable with the control unit so as to receive and store the representative value.

12. The device according to claim 1, further comprising a signaller configured to alert a user to an error condition of the device, said error condition being determined by a malfunctioning of the measurement sensor, said signaller comprising at least one among: an optical signaller, an acoustic signaller and a vibration motor.

13. The device according to claim 1, further comprising at least one mouthpiece attachment reversibly couplable to the mouthpiece.

14. The device according to claim 1, further comprising at least one filter interposed between the mouthpiece and the central chamber and/or between the central chamber and at least one among the inhalation chamber and the exhalation chamber.

15. The device according to claim 1, interfaceable with a remote database, in order to store the representative value and acquire from said remote database one or more items of operational information, said operational information comprising at least one training regime defined at least by a number of uses of the device in a predetermined interval of time and/or by the load configuration for each use.

16. The device according to claim 15, wherein the control unit is configured to compare the representative value with one or more predetermined threshold values representative of usage parameters of the device and to generate an alert signal as a function of said comparison.

* * * * *